US011529386B2

(12) United States Patent
Talbott

(10) Patent No.: US 11,529,386 B2
(45) Date of Patent: Dec. 20, 2022

(54) NUTRITIONAL SUPPLEMENTS AND METHODS OF NUTRITIONAL SUPPLEMENTATION AFFECTING MOOD AND FOCUS IN CHILDREN

(71) Applicant: Amare Global, Irvine, CA (US)

(72) Inventor: Shawn M. Talbott, Draper, UT (US)

(73) Assignee: AMARE GLOBAL, Irvine, CA (US)

( * ) Notice: Subject to any disclaimer, the term of this patent is extended or adjusted under 35 U.S.C. 154(b) by 0 days.

(21) Appl. No.: 17/013,212

(22) Filed: Sep. 4, 2020

(65) Prior Publication Data
US 2021/0060112 A1 Mar. 4, 2021

Related U.S. Application Data

(60) Provisional application No. 62/895,912, filed on Sep. 4, 2019.

(51) Int. Cl.
| | |
|---|---|
| *A61K 36/53* | (2006.01) |
| *A61K 36/88* | (2006.01) |
| *A61P 25/00* | (2006.01) |
| *A61K 36/61* | (2006.01) |
| *A61K 31/702* | (2006.01) |
| *A61K 36/537* | (2006.01) |

(52) U.S. Cl.
CPC ............ *A61K 36/88* (2013.01); *A61K 31/702* (2013.01); *A61K 36/53* (2013.01); *A61K 36/537* (2013.01); *A61K 36/61* (2013.01); *A61P 25/00* (2018.01)

(58) Field of Classification Search
None
See application file for complete search history.

(56) References Cited

U.S. PATENT DOCUMENTS

| | | |
|---|---|---|
| 7,781,572 B2 | 8/2010 | Bartlett et al. |
| 7,794,761 B2 | 9/2010 | Shelby et al. |
| 9,028,890 B2 | 5/2015 | Ferrari et al. |
| 9,700,071 B2 | 7/2017 | Silver et al. |
| 10,213,471 B1 | 2/2019 | Buckner |
| 10,449,148 B2 | 10/2019 | Gutierrez et al. |
| 2003/0206972 A1 | 11/2003 | Babish et al. |
| 2007/0269541 A1 | 11/2007 | Rohdewald |
| 2009/0148433 A1 | 6/2009 | Naidu et al. |
| 2011/0206649 A1 | 8/2011 | Bergonzelli et al. |
| 2011/0262618 A1 | 10/2011 | Melwitz |
| 2013/0064803 A1 | 3/2013 | Naidu et al. |
| 2013/0261183 A1 | 10/2013 | Bhagat |
| 2016/0000854 A1 | 1/2016 | Osborne et al. |
| 2019/0183849 A1 | 6/2019 | Kariman |
| 2020/0297605 A1 | 9/2020 | Ambrogio et al. |
| 2020/0352206 A1* | 11/2020 | Wagner-Salvini ........ A23L 2/54 |
| 2020/0397711 A1* | 12/2020 | Lee ..................... A61K 9/1075 |
| 2021/0069280 A1 | 3/2021 | Talbott |
| 2021/0121490 A1* | 4/2021 | Takahashi ............... A61P 25/28 |

FOREIGN PATENT DOCUMENTS

| | | |
|---|---|---|
| CN | 106615516 A | 5/2017 |
| WO | 03/21515 A2 | 3/2003 |
| WO | 2014/083438 A2 | 6/2014 |
| WO | 2015/006646 A1 | 1/2015 |
| WO | 2015/153841 A1 | 10/2015 |
| WO | 2018/013871 A1 | 1/2018 |
| WO | 2018/027070 A1 | 2/2018 |
| WO | 2018/035212 A1 | 2/2018 |
| WO | 2018/195097 A1 | 10/2018 |
| WO | 2019/056129 A2 | 3/2019 |
| WO | 2019/069096 A1 | 4/2019 |
| WO | 2019/078005 A1 | 4/2019 |
| WO | 2019/090273 A2 | 5/2019 |

OTHER PUBLICATIONS

Jiang, T. Health Benefits of Culinary Herbs and Spices J of AOAC Int 102(2)395-411 Mar./Apr. 2019. (Year: 2019).*
Sreedhar A. et al. Next-Gen Therapeutics for Skin Cancer: Nutraceuticals Nutrition and Cancer 70(5)697-709 Jul. 2019. (Year: 2019).*
Sorndech, W. et al. Isomalto-Oligosaccharides: Recent Insights in Production Technology and Their Use for Food and Medical Applications. Food Science and Technology 95:135-142, 2018. (Year: 2018).*
"International Search Report and Written Opinion of the International Searching Authority," issued in connection with Int'l Appl. No. PCT/US18/48945, dated Nov. 21, 2018 (7 pages).
"International Search Report and Written Opinion of the International Searching Authority," issued in connection with Int'l Appl. No. PCT/US18/48980, dated Nov. 30, 2018 (7 pages).
"International Search Report and Written Opinion of the International Searching Authority," issued in connection with Int'l Appl. No. PCT/US20/49469 dated Dec. 10, 2020 (8 pages).
"International Search Report and Written Opinion of the International Searching Authority," issued in connection with Int'l Appl. No. PCT/US20/49545, dated Dec. 10, 2020 (14 pages).
"International Search Report and Written Opinion of the International Searching Authority," issued in connection with Int'l Appl. No. PCT/US20/49555, dated Dec. 21, 2020 (13 pages).
"International Search Report and Written Opinion of the International Searching Authority," issued in connection with Int'l Appl. No. PCT/US20/49560, dated Jan. 7, 2021 (8 pages).
Amare Global, product names Sleep+, p. 2, Key Ingredients, Clinical Study at 2013, https://www.amare.com/corporate/SleepPlus, 1 page; retrieved Feb. 21, 2020.
Ambati, R. et al. Astaxanthin: Sources, Extraction, Stability, Biological Activities and its Commercial Applications—A Review. Marine Drugs 12:128-152, 2014. (Year: 2014).
Frotela-Saseta et al. (2011) Phytother. Res. 25: 1870-1875. (Year: 2011).

(Continued)

*Primary Examiner* — Ralph J Gitomer
(74) *Attorney, Agent, or Firm* — Holland & Hart LLP

(57) ABSTRACT

Nutritional supplements and methods of nutritional supplementation that affect focus and mental performance while supporting mood in subjects, including children, are provided. The supplements and methods of supplementation improve focus and/or mental performance by supporting both brain and gut health. In some instances, the nutritional supplements and methods of nutritional supplementation described affect both mood and focus in children simultaneously.

24 Claims, 1 Drawing Sheet

(56) References Cited

OTHER PUBLICATIONS

Ji, X. et al. Astaxanthin Improves Cognitive Performance in Mice . . . Brain Research 1659:88-95, 2017. (Year: 2017).
Kapoor et al. (2009) J. Agric. Food Chem. 57: 5358-5364. (Year: 2009).
Kaur et al. (2008) Nutr. Cancer 60(Suppl. 1): 2-11. (Year: 2008).
Kiralan et al. (2014) Industrial Crops and Products 57: 52-58. (Year: 2014).
Ku et al. (2008) Wood Sci. Technol. 42; 47-60. (Year: 2008).
Lizarraga et al. (2007) FEBS Journal 274: 4802-4811. (Year: 2007).
Lotterodt et al. (2010) LWT-Food Science and Technology 43: 1409-1413. (Year: 2010).
McGann et al. (2007) Food and Chemical Toxicology 45: 1224-1230. (Year: 2007).
Nature's Plus, Ageless Mood Support, title, p. 1, Supplement Facts, Apr. 27, 2015, https://www.amazaon.com/Natrues-Plus-Ageloss-Mood-Support/dp/B00CELG1XI; r1 page, retrieved Feb. 21, 2020.
Radhakrishnan et al. (2011) Frontiers in Bioscience E3, 1509-1523. (Year: 2011).
Raskin et al. (2004) Current Pharmaceutical Design, 10: 3419-3429. (Year: 2004).
Reagan-Shaw et al. (2010) Nutrition and Cancer 62(4): 517-524. (Year: 2010).
Revilla et al. (1998) J. Agric. Food Chem. 46: 4592-4597. (Year: 1998).
Rohdewald (2002) Intern. J. Clin. Pharmacol. Ther. vol. 40, No. 4: (158-168). (Year: 2002).
Schauss A. Advances in the Study of the Health Benefits and Mechanisms of Action of the Pulp and Seed of the Amazonian Palm Fruit, *Euterpe oleracea* Mart. Known as Acai. Chapter 10 of Fruits, Vegetables and Herbs, 2016. (Year: 2016).
Speranza et al., "Astaxanthin Treatment Reduced Oxidative Induced Pro-Inflammatory Cytokines Secretion in U937: SHP-1 as a Novel Biological Target", Marine Drugs, vol. 20, Issue 4, Apr. 2012, pp. 890-899.
Talbott et al. "Effect of coordinated probiotic/prebiotic/phytobiotic supplementation on microbiome balance and psychological mood state in healthy stressed adults" Functional Foods in Health and Disease, Apr. 30, 2019; 9(4): 265-275.
Talbott, S. et al. "Effect of Monocot Grass Extract on mood state and sleep patterns in moderately stress subjects", J Int Soc Sports Nutr. 2013, 10 (Suppl 1): p. 26. (Year: 2013).
University of Wisconsin School of Medicine and Health (Non-Pharmaceutical Approaches for Depression Towards Vitality, Pearls for Clinicians, Mar. 12, 2007). (Year: 2007).
Veeriah et al. (2006) Molecular Carcinogenesis 45:164-174. (Year: 2006).
Yamashita, E. Let Astaxanthin Be Thy Medicine PharmaNutrition 3:115-122, 2015. (Year: 2015).
Kristin Schmidt, Philip J. Cowen, Catherine J. Harmer, George Tzortzis, Steven Errington, Philip W. J. Burnet, Prebiotic intake reduces the waking cortisol response and alters emotional bias in healthy volunteers, 2015, Psychopharmacology, vol. 232, pp. 1793-1801 (Year: 2015).
L.M. Foster, T.A. Tompkins and W.J. Dahl, A comprehensive post-market review of studies on a probiotic product containing Lactobacillus helveticus R0052 and Lactobacillus rhamnosus R0011, 2011, Beneficial Microbes, vol. 2, Issue 4, pp. 319-334 (Year: 2011).
Michael Messaoudi et al., Beneficial psychological effects of a probiotic formulation (Lactobacillus helveticus R0052 and Bifidobacterium longum R0175) in healthy human volunteers, 2011, Gut Microbes, vol. 2, No. 4, pp. 256-261 (Year: 2011).

\* cited by examiner

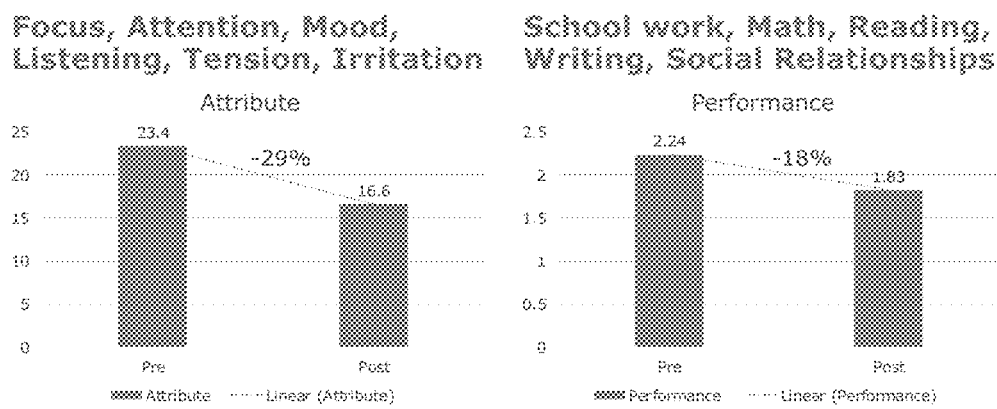

NUTRITIONAL SUPPLEMENTS AND METHODS OF NUTRITIONAL SUPPLEMENTATION AFFECTING MOOD AND FOCUS IN CHILDREN

BACKGROUND

The following relates generally to nutritional supplements and to methods of nutritional supplementation of subjects. More specifically, the following relates to nutritional supplements affecting mood and focus in subjects, including children, and to methods of supplementation of such subjects to improve focus and mental performance.

Many people struggle with focus and mental performance in a variety of settings, including the home, work, school, and sports. Children are especially affected by lack of focus and impaired mental performance. For many children, these conditions lead to behavioral problems, impulsivity, and/or hyperactivity. Concerned parents, educators, and caregivers employ a wide variety of behavioral techniques to help manage this, but some children fail to respond to these techniques.

Children who struggle with lack of focus and reduced mental performance in this way may face increased pressure at home, school, or in their extracurricular activities. They may experience ridicule from their peers. Some lose self-esteem, fall behind in their studies or activities, and struggle in their relationships.

Many individuals, including children, would benefit from nutritional supplements and methods of nutritional supplementation which improve focus and mental performance, and support mood. In some cases, it would be beneficial to provide nutritional supplements and methods of nutritional supplementation which are beneficial to focus and mental performance by nourishing brain and gut health.

SUMMARY

This application discloses improved nutritional supplements and methods of nutritional supplementation that affect focus and mental performance while supporting mood. Generally, the described techniques provide for unique nutritional supplements and methods for their use to improve focus and/or mental performance by supporting both brain and gut health. In some instances, the nutritional supplements and methods of nutritional supplementation described affect both mood and focus in children simultaneously.

A method for improving focus and/or mental performance in a subject is described. The method may include administering to the subject an effective amount of a composition including saffron stigma extract, holy basil leaf extract, rosemary leaf extract, oregano leaf extract, clove flower extract, and prebiotic fiber.

In some examples of the method described herein, the saffron stigma extract may be obtained from *Crocus sativus* L.

In some examples of the method described herein, the holy basil leaf extract may be obtained from *Ocimum sanctum*.

In some examples of the method described herein, the rosemary leaf extract may be obtained from *Rosmarinus officinalis*.

In some examples of the method described herein, the oregano leaf extract may be obtained from *Origanum vulgare*.

In some examples of the method described herein, the clove flower extract may be obtained from *Syzygium aromaticum*.

In some examples of the method described herein, the prebiotic fiber includes isomaltooligosaccharide.

Some examples of the method of supplementation described herein further include the step of identifying a subject in need of improvement of focus and/or mental performance. In some of these methods, identifying a subject in need of improvement of focus and/or mental performance may include identifying a subject in need of at least one of improvement of attention, mood, and/or listening; and/or in need of a reduction in tension and/or irritation.

In some examples of the method described herein, identifying a subject in need of improvement of focus and/or mental performance includes identifying a subject in need of at least one of improvement of mental performance, as measured by improved performance in school work. In some instances, this may be measured using the NICHQ survey developed by the American Academy of Pediatrics and National Initiative for Children's Healthcare Quality.

Methods for improving symptoms of focus and/or mental performance in a subject are described. The methods may include administering to the subject an effective amount of a composition including approximately 14 mg of saffron stigma extract, approximately 10 mg of holy basil leaf extract, approximately 10 mg of rosemary leaf extract, approximately 10 mg of oregano leaf extract, approximately 10 mg of clove flower extract, and approximately 10 mg of approximately 2.5 g of prebiotic fiber.

In some examples of the methods described herein, the compositions may include from about 10 to about 20 mg of saffron stigma extract, from about 12 to about 16 mg of saffron stigma extract, or about 14 mg of saffron stigma extract. In some examples, the saffron stigma extract may be obtained from *Crocus sativus* L.

In some examples of the methods described herein, the compositions may include from about 5 to about 20 mg of holy basil leaf extract, from about 7 to about 16 mg of holy basil leaf extract, or about 10 mg holy basil leaf extract. In some examples of the methods described herein, the holy basil leaf extract may be obtained from *Ocimum sanctum*.

In some examples of the methods described herein, the compositions may include from about 5 to about 20 mg of rosemary leaf extract, from about 7 to about 16 mg of rosemary leaf extract, or about 10 mg rosemary leaf extract. In some examples of the methods described herein, the rosemary leaf extract may be obtained from *Rosmarinus officinalis*.

In some examples of the methods described herein, the compositions may include from about 5 to about 20 mg of oregano leaf extract, from about 7 to about 16 mg of oregano leaf extract, or about 10 mg oregano leaf extract. In some examples of the methods described herein, the oregano leaf extract may be obtained from *Origanum vulgare*.

In some examples of the methods described herein, the compositions may include from about 5 to about 20 mg of clove flower extract, from about 7 to about 16 mg of clove flower extract, or about 10 mg clove flower extract. In some examples of the methods described herein, the clove flower extract may be obtained from *Syzygium aromaticum*.

In some examples of the methods described herein, the prebiotic fiber includes isomaltooligosaccharide.

Further, some examples of the methods described herein include the step of identifying a subject in need of improvement of focus and/or mental performance. In such methods, identifying a subject in need of improvement of focus and/or mental performance may include identifying a subject in need of at least one of improvement of attention, mood, and/or listening; and/or a reduction in tension and/or irritation.

In some examples of the method described herein, identifying a subject in need of improvement of focus and/or mental performance includes identifying a subject in need of at least one of improvement of mental performance, as measured by improved performance in concentrated mental labor such as school work.

In some examples of the method described herein, identifying a subject in need of improvement of focus and/or mental performance is identification of a child in need of such improvement. A child may have need of improvement of focus and/or mental performance, and such a need may be measured by improved performance on schoolwork, such as, without limitation, mathematics, reading and/or writing. Alternatively, a child in need of improvement of focus and/or mental performance may be identified by a survey such as the NICHQ survey developed by the American Academy of Pediatrics and the National Initiative for Children's Healthcare Quality.

In other situations, identifying a subject in need of improvement of focus and/or mental performance may include identifying a subject with difficulty in establishing, developing or maintaining social relationships. In some of these, the method includes identifying a child with difficulty in establishing, developing or maintaining social relationships.

Still other methods for improving symptoms of focus and/or mental performance in a subject are described. The methods may include administering to the subject an effective amount of a composition including approximately 14 mg of saffron stigma extract obtained from *Crocus sativus* L., approximately 10 mg of Tulsi holy basil leaf extract obtained from *Ocimum sanctum*, approximately 10 mg of rosemary leaf extract obtained from *Rosmarinus officinalis*, approximately 10 mg of oregano leaf extract obtained from *Origanum vulgare*, approximately 10 mg of clove flower extract obtained from *Syzygium aromaticum*, and approximately 2.5 g of isomaltooligosaccharide.

Some examples of the methods further include the step of identifying a subject in need of improvement of focus and/or mental performance. This step may include identifying a subject in need of at least one of improvement of attention, mood, and/or listening; and/or a reduction in tension and/or irritation.

In some examples of the methods, identifying a subject in need of improvement of focus and/or mental performance includes identifying a subject in need of at least one of improvement of mental performance, as measured by improved performance in school work.

In some examples of the method described herein, identifying a subject in need of improvement of focus and/or mental performance is identification of a child. A child may have need of improvement of focus and/or mental performance, and such a need may be measured by improved performance on schoolwork, such as, without limitation, mathematics, reading and/or writing. Alternatively, a child in need of improvement of focus and/or mental performance may be identified by a survey such as the NICHQ survey developed by the American Academy of Pediatrics and the National Initiative for Children's Healthcare Quality.

BRIEF DESCRIPTION OF THE DRAWINGS

FIG. 1 is a table showing the effects of supplementation with the nutritional supplements of the present disclosure on mood in children, as measured by effects on focus, attention, mood, listening, tension and irritation; and on school work, math, reading, writing and social relationships.

DETAILED DESCRIPTION

As used herein, treatment means any manner in which the symptoms or pathology of a condition, disorder or disease are ameliorated or otherwise beneficially altered. Treatment also encompasses any pharmaceutical use of the compositions herein.

The supplement compositions of this disclosure may be administered in a variety of suitable dosage forms, including, without limitation, tablets, capsules, granules, powders, liquids, liposome inclusions, ointments, gels, external powders, sprays, inhalable powders, injectable preparations (solutions, suspensions, emulsions, solids to be dissolved when used, etc.), eye drops, eye ointments, suppositories, and the like can be selected appropriately depending on the administration method, and the compositions of the present disclosure can be accordingly formulated. Formulation in general is described in references including Comprehensive Medicinal Chemistry, Volume 5, Editor Hansch et al, Pergamon Press 1990.

As used herein, any range set forth is inclusive of the end points of the range unless otherwise stated.

As used herein, "effective amount" refers to an amount of a substance which is sufficient to achieve its intended purpose or effect. Various biological factors may affect the ability of a delivered substance to perform its intended task. Therefore, an "effective amount" may be dependent on such biological factors. An effective amount of a compound for treating a disorder is an amount that is sufficient to ameliorate, or in some manner reduce a symptom or stop or reverse progression of a condition. Such amount may be administered as a single dosage or may be administered according to a regimen whereby it is effective. The achievement of therapeutic effects may be measured by a physician or other qualified medical personnel using evaluations known in the art, (for example with testosterone supplementation therapy, physical examination, blood and saliva tests may be used), it is recognized that individual variation and response to treatments may make the achievement of therapeutic effects a subjective decision.

Further, determination of the effectiveness of the amount is well within the knowledge and ability of one of ordinary skill in the art.

As used herein, "administration," and "administering" may be used interchangeably, and refer to the act of presenting, applying, or introducing a drug to a subject in order to achieve a desired physiological or psychological response.

As used herein, amelioration of the symptoms of a particular disorder by administration of a particular pharmaceutical composition refers to any lessening, whether permanent or temporary, lasting or transient that can be attributed to or associated with administration of the composition.

As noted above, many individuals, and in some cases, many children, struggle to build and/or maintain adequate focus and mental performance to be successful in a variety of settings. Although most often highlighted in a school setting, lack of focus and/or mental performance can become a detriment to an individual such as a child in the home, at work, and in extracurricular activities such as sports or music, as well.

Children's issues with focus and mental performance have been the subject of research and discussion for many years. In recent years, much attention has been devoted to this subject as pharmaceutical interventions have become available, and parents, educators and physicians have worked to understand when or if such interventions are in a child's best interests.

Children tend to be especially affected by issues with focus and impaired mental performance which can develop into behavioral problems, impulsivity, and/or hyperactivity.

These problems may increase stress and unhappiness at home, school, or in their extracurricular activities. Reduced performance in school, or in other activities important to them may damage their self-esteem, subject them to unwanted attention from parents or teachers, invoke criticism from peers, and cause them to fall behind.

This disclosure provides nutritional supplements and methods of nutritional supplementation which improve focus and mental performance, and support mood. In some instances this is accomplished by nourishing both the brain and the gut, which has been observed herein to provide much wider than expected benefits to focus and mental performance than observed with current nutritional supplements and methods of nutritional supplementation.

Improved nutritional supplements and methods of nutritional supplementation are disclosed that affect focus and mental performance while supporting mood. Generally, the described techniques provide for unique nutritional supplements and methods for their use to improve focus and/or mental performance by supporting both brain and gut health. In some instances, the nutritional supplements and methods of nutritional supplementation described affect both mood and focus in individuals such as children simultaneously.

Methods for improving focus and/or mental performance in a subject may include administering to the subject an effective amount of a composition including saffron stigma extract, holy basil leaf extract, rosemary leaf extract, oregano leaf extract, clove flower extract, and prebiotic fiber.

In some examples of the method described herein, the saffron stigma extract may be obtained from *Crocus sativus* L.

In some examples of the method described herein, the holy basil leaf extract may be obtained from *Ocimum sanctum*.

In some examples of the method described herein, the rosemary leaf extract may be obtained from *Rosmarinus officinalis*.

In some examples of the method described herein, the oregano leaf extract may be obtained from *Origanum vulgare*.

In some examples of the method described herein, the clove flower extract may be obtained from *Syzygium aromaticum*.

In some examples of the method described herein, the prebiotic fiber includes isomaltooligosaccharide.

Other species of *Crocus*, basil, rosemary, oregano and/or clove may be suitable within the scope of the present disclosure.

Some examples of the method of supplementation described herein further include the step of identifying a subject in need of improvement of focus and/or mental performance. In some of these methods, identifying a subject in need of improvement of focus and/or mental performance may include identifying a subject in need of at least one of improvement of attention, mood, and/or listening; and/or in need of a reduction in tension and/or irritation.

In some examples of the method described herein, identifying a subject in need of improvement of focus and/or mental performance includes identifying a subject in need of at least one of improvement of mental performance, as measured by improved performance in school work. In some instances, this may be measured using the NICHQ survey developed by the American Academy of Pediatrics and National Initiative for Children's Healthcare Quality.

Methods for improving symptoms of focus and/or mental performance in a subject are described. The methods may include administering to the subject an effective amount of a composition including approximately 14 mg of saffron stigma extract, approximately 10 mg of holy basil leaf extract, approximately 10 mg of rosemary leaf extract, approximately 10 mg of oregano leaf extract, approximately 10 mg of clove flower extract, and approximately 10 mg of approximately 2.5 g of prebiotic fiber.

In some examples of the methods described herein, the saffron stigma extract may be obtained from *Crocus sativus* L.

In some examples of the methods described herein, the holy basil leaf extract may be obtained from *Ocimum sanctum*.

In some examples of the methods described herein, the rosemary leaf extract may be obtained from *Rosmarinus officinalis*.

In some examples of the methods described herein, the oregano leaf extract may be obtained from *Origanum vulgare*.

In some examples of the methods described herein, the clove flower extract may be obtained from *Syzygium aromaticum*.

In some examples of the methods described herein, the prebiotic fiber includes isomaltooligosaccharide.

Further, some examples of the methods described herein include the step of identifying a subject in need of improvement of focus and/or mental performance. In such methods, identifying a subject in need of improvement of focus and/or mental performance may include identifying a subject in need of at least one of improvement of attention, mood, and/or listening; and/or a reduction in tension and/or irritation.

In some examples of the method described herein, identifying a subject in need of improvement of focus and/or mental performance includes identifying a subject in need of at least one of improvement of mental performance, as measured by improved performance in concentrated mental labor such as school work.

In some examples of the method described herein, identifying a subject in need of improvement of focus and/or mental performance is identification of a child in need of such improvement. A child may have need of improvement of focus and/or mental performance, and such a need may be measured by improved performance on schoolwork, such as, without limitation, mathematics, reading and/or writing. Alternatively, a child in need of improvement of focus and/or mental performance may be identified by a survey such as the NICHQ survey developed by the American Academy of Pediatrics and the National Initiative for Children's Healthcare Quality.

In other situations, identifying a subject in need of improvement of focus and/or mental performance may include identifying a subject with difficulty in establishing, developing or maintaining social relationships. In some of these, the method includes identifying a child with difficulty in establishing, developing or maintaining social relationships.

Still other methods for improving symptoms of focus and/or mental performance in a subject are described. The methods may include administering to the subject an effective amount of a composition including approximately 14 mg of saffron stigma extract obtained from *Crocus sativus* L., approximately 10 mg of Tulsi holy basil leaf extract obtained from *Ocimum sanctum*, approximately 10 mg of rosemary leaf extract obtained from *Rosmarinus officinalis*, approximately 10 mg of oregano leaf extract obtained from *Origanum vulgare*, approximately 10 mg of clove flower extract obtained from *Syzygium aromaticum*, and approximately 2.5 g of isomaltooligosaccharide.

Some examples of the methods further include the step of identifying a subject in need of improvement of focus and/or mental performance. This step may include identifying a subject in need of at least one of improvement of attention, mood, and/or listening; and/or a reduction in tension and/or irritation.

In some examples of the methods, identifying a subject in need of improvement of focus and/or mental performance includes identifying a subject in need of at least one of improvement of mental performance, as measured by improved performance in school work.

In some examples of the method described herein, identifying a subject in need of improvement of focus and/or mental performance is identification of a child. A child may have need of improvement of focus and/or mental performance, and such a need may be measured by improved performance on schoolwork, such as, without limitation, mathematics, reading and/or writing. Alternatively, a child in need of improvement of focus and/or mental performance may be identified by a survey such as the NICHQ survey developed by the American Academy of Pediatrics and the National Initiative for Children's Healthcare Quality.

It should be noted that the methods described herein describe possible implementations, and that the operations and the steps may be rearranged or otherwise modified and that other implementations are possible. Further, aspects from two or more of the methods may be combined.

EXAMPLE 1

Experimental Design

A study was conducted to explore the effects of supplementation using supplements and methods of supplementation according to the present disclosure. A test group of 10 children between the ages of 6-12 were recruited to participate in the study. Each was seen as on the border between needing/not needing to be medicated with drugs such as Ritalin for ADHD or Prozac for depression.

The study subjects underwent nutritional supplementation with a nutritional supplement. The supplement was a 54-mg blend of 14 mg of saffron stigma extract from *Crocus sativus* L., 10 mg of Tulsi Holy Basil (*Ocimum sanctum*) leaf extract, 10 mg of rosemary (*Rosmarinus officinalis*) leaf extract, 10 mg of oregano (*Origanum vulgare*) leaf extract, and 10 mg of clove (*Syzygium aromaticum*) flower extract in a base of 2.5 grams of a prebiotic fiber base of isomaltooligosaccharide. Supplementation was conducted for a period of 30 days. The supplement was presented to the subjects as a "direct-to-mouth powder" administered orally once-daily.

The results are indicated below as averages:

TABLE 1

| | |
|---|---|
| Focus/mood symptoms: (focus, attention, mood, listening, tension, irritation) | +29% improvement |
| Mental performance: | +18% improvement |

As noted, study subjects were observed to show a +29% improvement in symptoms of focus and/or mood, including improved focus, attention, mood, listening, tension and/or irritation. Further, subjects showed a +18% improvement in mental performance in things such as schoolwork (such as, without limitation, mathematics, reading, writing), as measured using the NICHQ survey developed by the American Academy of Pediatrics and the National Initiative for Children's Healthcare Quality.

As used herein, including in the claims, "or" as used in a list of items (e.g., a list of items prefaced by a phrase such as "at least one of" or "one or more of" indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

In the appended FIGURES, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label, or other subsequent reference label.

The description set forth herein describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method of improving focus and/or mental performance in a subject in need thereof, the method comprising:
administering to the subject an effective amount of a direct-to-mouth powder composition by administering the direct-to-mouth powder composition to the subject orally, the direct-to-mouth powder composition comprising:
saffron stigma extract;
holy basil leaf extract;
rosemary leaf extract;
oregano leaf extract;
clove flower extract; and
prebiotic fiber.

2. The method of claim 1, wherein the saffron stigma extract is obtained from *Crocus sativus* L.

3. The method of claim 1, wherein the holy basil leaf extract is obtained from *Ocimum* sanctum.

4. The method of claim 1, wherein the rosemary leaf extract is obtained from *Rosmarinus officinalis*.

5. The method of claim 1, wherein the oregano leaf extract is obtained from *Origanum vulgare*.

6. The method of claim 1, wherein the clove flower extract is obtained from *Syzygium aromaticum*.

7. The method of claim 1, wherein the prebiotic fiber includes isomaltooligosaccharide.

8. The method of claim 1, further including the step of identifying a subject in need of improvement of focus and/or mental performance.

9. The method of claim 8, wherein identifying a subject in need of improvement of focus and/or mental performance includes identifying a subject in need of at least one of improvement of attention, mood, and/or listening; and/or a reduction in tension and/or irritation.

10. The method of claim 8, wherein identifying a subject in need of improvement of focus and/or mental performance includes identifying a subject in need of at least one of improvement of mental performance, as measured by improved performance in school work.

11. A method of improving symptoms of focus and/or mental performance in a subject in need thereof, the method comprising:
administering to the subject an effective amount of a direct-to-mouth powder composition by administering the direct-to-mouth powder composition to the subject orally, the direct-to-mouth powder composition comprising:
approximately 14 mg of saffron stigma extract;
approximately 10 mg of holy basil leaf extract;
approximately 10 mg of rosemary leaf extract;
approximately 10 mg of oregano leaf extract;
approximately 10 mg of clove flower extract; and
approximately 2.5 g of prebiotic fiber.

12. The method of claim 11, wherein the saffron stigma extract is obtained from *Crocus sativus* L.

13. The method of claim 11, wherein the holy basil leaf extract is obtained from *Ocimum* sanctum.

14. The method of claim 11, wherein the rosemary leaf extract is obtained from *Rosmarinus officinalis*.

15. The method of claim 11, wherein the oregano leaf extract is obtained from *Origanum vulgare*.

16. The method of claim 11, wherein the clove flower extract is obtained from *Syzygium aromaticum*.

17. The method of claim 11, wherein the prebiotic fiber includes isomaltooligosaccharide.

18. The method of claim 11, further including the step of identifying a subject in need of improvement of focus and/or mental performance.

19. The method of claim 18, wherein identifying a subject in need of improvement of focus and/or mental performance includes identifying a subject in need of at least one of improvement of attention, mood, and/or listening; and/or a reduction in tension and/or irritation.

20. The method of claim 18, wherein identifying a subject in need of improvement of focus and/or mental performance includes identifying a subject in need of at least one of improvement of mental performance, as measured by improved performance in school work.

21. A method of improving symptoms of focus and/or mental performance in a subject in need thereof, the method comprising:
administering to the subject an effective amount of a direct-to-mouth powder composition by administering the direct-to-mouth powder composition to the subject orally, the direct-to-mouth powder composition comprising:
approximately 14 mg of saffron stigma extract obtained from *Crocus sativus* L.;
approximately 10 mg of Tulsi holy basil leaf extract obtained from *Ocimum* sanctum;
approximately 10 mg of rosemary leaf extract obtained from *Rosmarinus officinalis;*
approximately 10 mg of oregano leaf extract obtained from *Origanum vulgare;*
approximately 10 mg of clove flower extract obtained from *Syzygium aromaticum*; and
approximately 2.5 g of isomaltooligosaccharide.

22. The method of claim 21, further including the step of identifying a subject in need of improvement of focus and/or mental performance.

23. The method of claim 22, wherein identifying a subject in need of improvement of focus and/or mental performance includes identifying a subject in need of at least one of improvement of attention, mood, and/or listening; and/or a reduction in tension and/or irritation.

24. The method of claim 22, wherein identifying a subject in need of improvement of focus and/or mental performance includes identifying a subject in need of at least one of improvement of mental performance, as measured by improved performance in school work.

* * * * *